United States Patent [19]

Moore

[11] 4,023,215

[45] May 17, 1977

[54] LOCKING PROSTHETIC KNEE

[76] Inventor: Robert R. Moore, 5401 San Leandro St., Oakland, Calif. 94601

[22] Filed: Feb. 17, 1976

[21] Appl. No.: 658,628

[52] U.S. Cl. .......................................... 3/26; 3/28; 3/29
[51] Int. Cl.² .......................... A61F 1/04; A61F 1/08
[58] Field of Search ............................... 3/22–29, 3/2, 1

[56] References Cited

UNITED STATES PATENTS

| 37,087 | 12/1862 | Cotty | 3/29 |
|---|---|---|---|
| 1,343,297 | 6/1920 | Worman | 3/29 X |
| 2,542,567 | 2/1951 | Peters | 3/28 |
| 2,794,987 | 6/1957 | Oliver | 3/26 |
| 3,440,668 | 4/1969 | Dachs et al. | 3/1 |

FOREIGN PATENTS OR APPLICATIONS

| 751,389 | 6/1933 | France | 3/26 |
|---|---|---|---|
| 342,833 | 10/1921 | Germany | 3/26 |

*Primary Examiner*—Ronald L. Frinks
*Attorney, Agent, or Firm*—Harris Zimmerman

[57] ABSTRACT

A prosthetic knee construction includes a single axis mechanism secured in a knee of rigid foam, wood, or similar material, and a leg shank pivotally secured to the lateral shaft of the mechanism. The shank is of hollow foam, wood, or similar construction, and includes a spaced pair of metal supports extending from the axis downwardly through the foam to a spool disposed in the middle of the shank. An elastic extension assist may be secured between the spool and the knee mechanism to resiliently urge the assembly toward full extension. The mechanism may be provided with a friction assembly impinging on the knee axis, and may be provided with a manually operated lock, as required according to the abilities and desires of the wearer.

2 Claims, 3 Drawing Figures

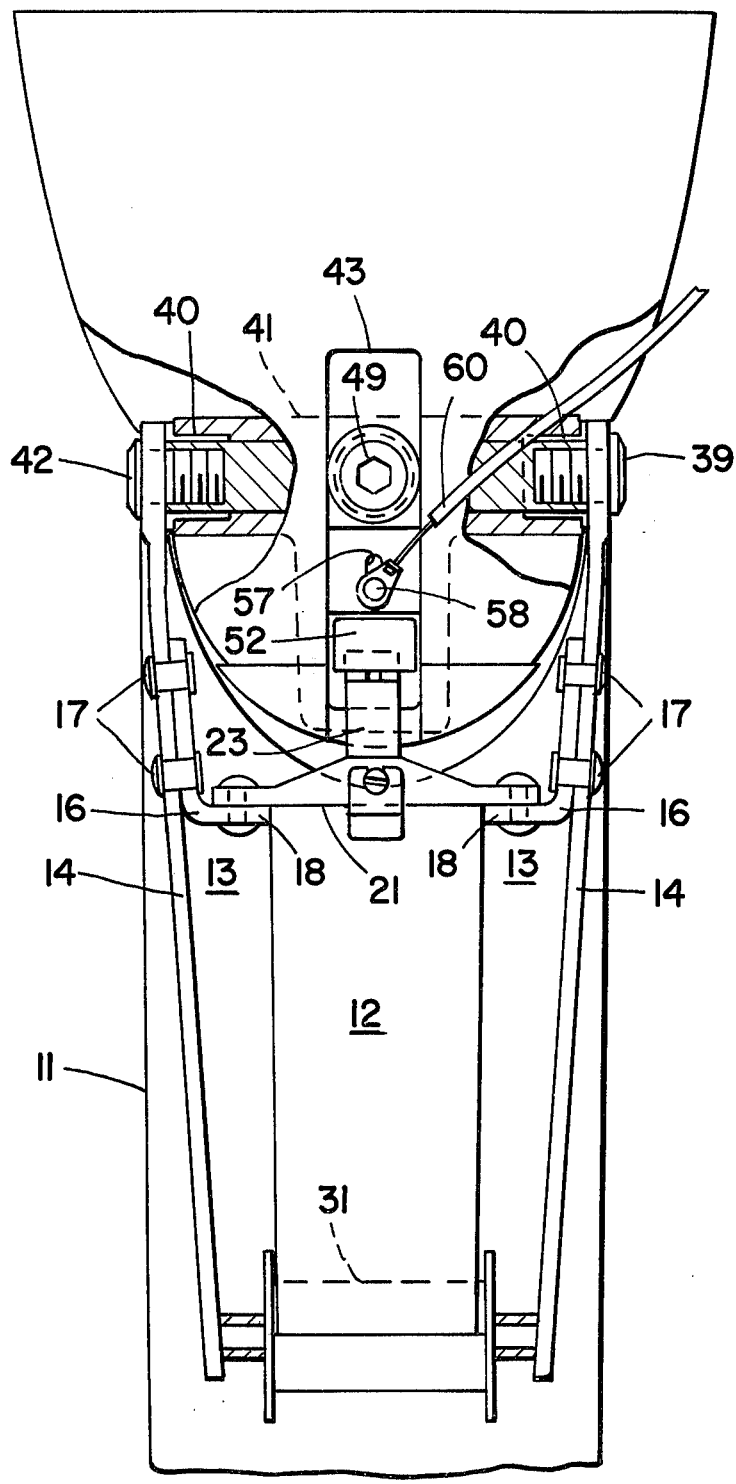
FIG_1

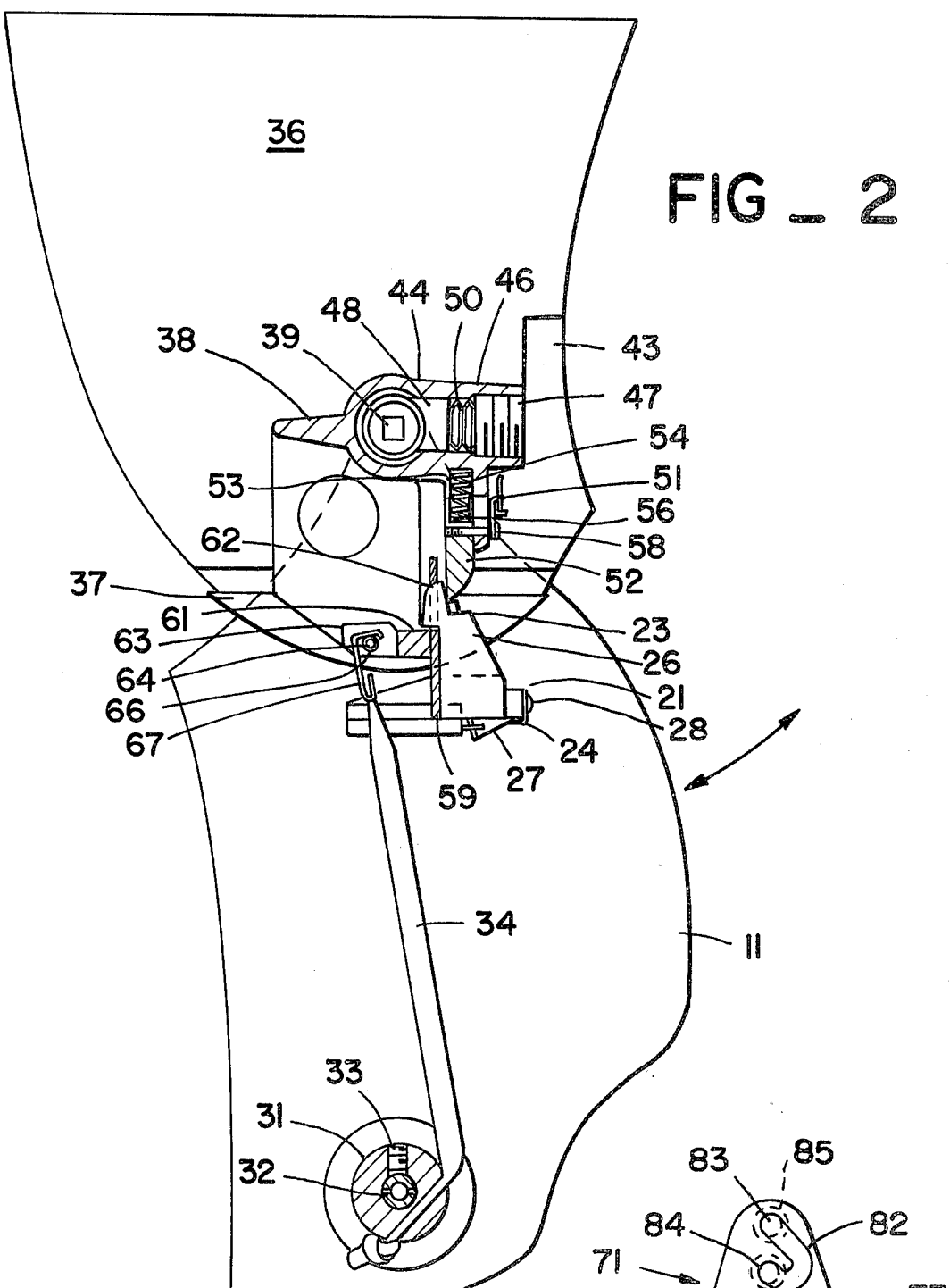
FIG_2
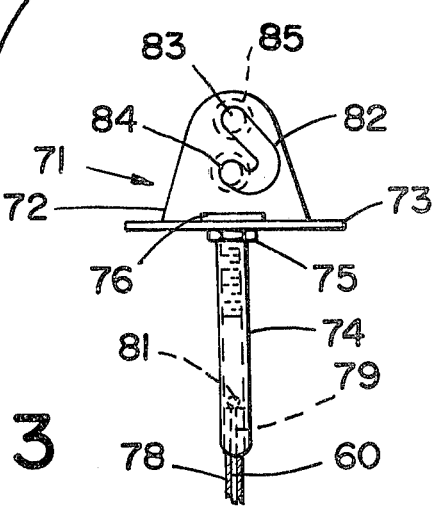
FIG_3

LOCKING PROSTHETIC KNEE

BACKGROUND OF THE INVENTION

There is known in the prosthetic arts myriad devices for replacing the human knee and for approximating its form and function. These prosthetic devices include simple single axis assemblies, single axis assemblies with friction, and various combinations of other features including extension assists, manual locks, automatic locks, and the like. All of these devices may be characterized by the fact that they are designed for only one purpose, and that they must be custom fitted for an individual.

For example, an amputee may be fitted with a prosthetic knee, such as a simple single axis knee. The prosthetic knee socket must be fitted to the individual with great care by a professional prosthetist, and the cost of the prosthetic knee and the professional services may be considerable. However, should the health of the individual improve or deteriorate, or should the agility of the individual change, or should the individual become accustomed to the prosthesis, it may no longer be sufficient for the needs of the wearer.

For example, an individual who learns to walk with proficiency with a simple single axis knee may find that as his or her health deteriorates, a locking knee is more desirable. This problem may be alleviated by the addition of a lock mechanism to the single axis knee, which is known in the art. Prior art prostheses, however, are not adapted easily to be fitted with additional features such as a locking mechanism. Thus the individual must purchase a new prosthesis with the desired features, thereby incurring substantial additional expense. Also, the fitting process must be reiterated, which is also costly.

SUMMARY OF THE INVENTION

The present invention generally comprises a single axis knee which is easily adapted to be modified to suit the changing requirements of the amputee. It includes a rigid foam hollow leg shank member which is provided with a pair of spaced support members extending upwardly in the side walls thereof to the journal for the single axis shaft. A detent extends upwardly from a base lock member which is bolted or rivetted to the support members near the upper ends thereof.

The knee member is formed of rigid foam material, in which is anchored the knee mechanism. The mechanism includes a sleeve through which the single axis shaft extends, and a friction shoe assembly, the latch engaging the detent of the shank member. The latch is controlled by a lanyard which extends out of the knee and upwardly to a position on the upper leg which is readily accessible to the hand of the wearer.

A spool is disposed across the cavity of the leg shank member, secured between the lower ends of the support members. An elastic extension assist may be secured between the spool and the mechanism of the knee member to resiliently urge the prosthesis toward full extension. It should be emphasized that the prosthesis of the present invention may be used as a simple single axis knee, as a single axis knee with friction, as a locking knee, as a single axis knee with the extension assist, or as a single axis knee with any combination of the foregoing. The function of the knee prosthesis can be adapted to suit the requirements of the wearer, either during or subsequent to the initial fitting of the prosthesis.

THE DRAWING

FIG. 1 is a rear cross-sectional elevation of the knee prosthesis of the present invention.

FIG. 2 is a side cross-sectional elevation of the knee prosthesis of the present invention.

FIG. 3 is a detailed view of the lanyard latch control for the present invention.

DESCRIPTION OF THE PREFERRED EMBODIMENT

With reference to FIGS. 1 and 2, the preferred embodiment includes a leg shank member 11 which is formed of a rigid foam material. The shank member includes a centrally disposed longitudinal cavity 12, into which a pair of spaced apart opposed shoulders 13 extend. A pair of steel reinforcing members 14 are anchored in spaced apart relationship with the foam walls of the shank member and extend substantially the entire length thereof. Joined to the reinforcing members are a pair of right angle members 16 secured in place by rivets 17. The legs 18 of the right angle members are directed inwardly and disposed to form the top surface of the shoulders 13.

Extending between the legs 18 of the right angle members and riveted thereto is a lock base plate 21. The base plate includes a detent 23 extending upwardly therefrom, as best shown in FIG. 2. The detent is provided with a clicker mechanism 24 which emits an audible sound when the latch first engages the detent. The clicker comprises a pin 26 which is slidably received in a hole extending through the base plate to the engagement surface of the detent. A resilient clicking member 27 impinges on the lower end of the pin 26, the clicking member being secured to the base plate by a screw 28.

The shank member may also be provided with an extension assist to bias the knee assembly toward full extension. The extension assist includes a spool 31 secured between the lower ends of the shoulders 13 in the cavity 12 and mounted on a shaft 32 extending through the shank and through the reinforcing members 14. The angular position of the spool is maintained by a set screw 33 disposed radially in the spool and impinging on shaft 32. Secured to the spool is an elastic extensible member 34 which extends upwardly through the cavity 12 and is secured at its upper end to the knee portion of the invention. The spool is rotated to adjust the tension of the member 34, and secured in the selected orientation by the set screw.

The knee member 36 of the invention is also formed of a rigid foam material, and includes a pad 37 at the lower tip thereof for absorbing shocks associated with kneeling and similar movements. The knee mechanism 38 is anchored in the foam material at the lower end of the knee member. The knee member is pivotally secured to the shank member by means of a bolt 39 which extends through holes in the upper ends of the reinforcing members 14, and through a sleeve 41 in the knee mechanism 38. The bolt is secured by a cap screw 42 received in the bolt, and bushings 40 are provided at either end for relieving friction between the bolt and the sleeve.

The knee member is provided with a longitudinal slot 43 in the lower end thereof. A friction shoe assembly 44 extends from the sleeve to the slot, and includes a housing 46 having a partially threaded hole 47 extending through the sleeve. If a friction effect is desired, a friction shoe 48 is disposed in the hole 47, backed up by four Belleville springs 50 arrayed in opposition. A socket head adjustment screw 49 is then threaded into the hole to adjust the impingement of the shoe on the bolt. If no friction effect is desired, the hole is merely plugged, awaiting any future use.

Depending from the friction housing 46 is a latch assembly 51, which includes a latch member 52 slidably received in a channel 53. A spring 54 under compression is disposed within a recess 56 in the latch member and the upper end of the channel, to urge the latch member toward the detent of the shank member. A slot 57 extends from the channel to the slot 43 in the knee member, and a screw 58 extends therethrough and is secured in the latch member. As shown in FIG. 1, the screw 58 secures a lanyard 60 or bowden cable to the latch for control purposes, as will be explained in the following description. The lanyard 60 may exit through the knee to the right or left, so that the prosthesis is adaptable for use on a left or right prosthesis.

The front surface of the detent is provided with an impact bumper 59, and the lower portion of the knee mechanism includes a block 61 for impinging on the bumper 59 as the knee assembly reaches full extension. At approximately the same position the latch clears the curved surface 62 of the detent and snaps into locking engagement with the detent. The latch also strikes the pin 26 which snaps the clicker to apprise the wearer that the leg is securely locked in the fully extended position. The engagement of the block 61 and the bumper 59 prevents any further extension of the knee, and the engagement of the latch and the detent prevents any genuflection of the knee.

The knee mechanism also includes provisions for securing the upper end of the extension assist member 34 to the knee member. The lower end of the mechanism is provided with a recess 63 across which extends a pin 64. A sleeve 66 is pivotally secured about the pin 64, and a bracket 67 is joined to the sleeve. The upper end of the elastic member is retained by the bracket, and is thus joined to the knee mechanism in freely pivoting fashion. As the knee is flexed the bracket pivots to eliminate any binding of the elastic member 34, and the member 34 is stretched to provide a resilient biasing force to return the knee to full extension.

The lanyard 60 extends through a sheath tube 78 to a latch control mechanism as shown in FIG. 3. The latch control comprises a bracket 71 having a planar arcuate member 72 and a narrow panel 73 extending perpendicularly therefrom. A cable adjustment tube 74 is secured to the panel 73 by a screw 76 extending therethrough and threadedly received in the tube 74. The upper end of the lanyard extends into the lower end of the adjustment tube, through a helical spring cable guide 79 to a cable tip 81. The spring provides resilience in the lanyard control to relieve stress. The tube 74 in conjunction with the screw 76 and a locking nut 75 is used to selectively vary the spacing between the cable end and the bracket 71.

The bracket member 72 is provided with a J-slot 82 which receives therethrough a screw or stud 85 extending from the upper leg prosthesis of the amputee. The J-slot provides two detent positions, 83 and 84, in which the screw 85 is retained by the tension in the lanyard. With the screw 85 retained in the position 84 the tension in the lanyard is increased sufficiently to pull the latch up and release the detent 26. In this position the knee thus will not lock, acting as a single axis, pivoting knee adapted for walking.

With the screw 85 retained in the position 83, the tension in the lanyard is not sufficient to release the latch. If the knee is in the flexed position, as when the wearer is sitting, the knee will lock as soon as it is fully extended, as when the wearer stands. Once locked at full extension, it will remain locked, as is common for a standard locking knee.

It must be emphasized that the prosthesis of the present invention is adaptable so that its features, such as the friction assembly, the extension assist, the latch, and the clicker assembly, are all optional. Any of these features may be added or removed as required by the wearer, either at the time of the initial fitting or at any subsequent time. Furthermore, the knee mechanism is disposed entirely in the knee portion of the prosthesis. This arrangement is advantageous in that the cable does not undergo any flexure or stress as the knee is flexed, unlike prior art devices. Also, the present invention relies on the combined structural strengths of the metal reinforcing members bonded in the foam material, thereby optimizing the strength-weight characteristic of the prosthesis.

I claim:

1. A knee prosthesis, comprising a knee member formed substantially of a rigid foam material, a knee mechanism secured in said knee member and including a lateral passage therethrough, a leg shank member formed substantially of rigid foam material, a pair of opposed reinforcing members anchored in the side walls of said shank member and extending from the top thereof to at least a medial portion thereof, the upper ends of said reinforcing members including aligned holes therethrough, a pivot member extending through said aligned holes and through said passage in said knee mechanism, a lock base plate extending laterally between the upper end portions of said reinforcing members, a detent member extending upwardly from said lock base plate, a latch assembly disposed in said knee mechanism; said latch assembly including a slot, a latch member disposed in said slot and translatable toward and resiliently biased toward engagement with said detent member, said knee mechanism including a friction shoe assembly adjacent to and communicating with said passage, a spool disposed within a medial portion of said shank member and secured between said reinforcing members, and elastic member extending between said spool and said knee mechanism, said spool being angularly adjustable to vary the tension in said elastic member.

2. The knee prosthesis of claim 1, further including bowden cable means secured to said latch member for translating said latch member into and out of engagement with said detent member.

* * * * *